United States Patent
Beaumont et al.

(10) Patent No.: US 10,593,487 B2
(45) Date of Patent: Mar. 17, 2020

(54) MIXED ORGANIC-INORGANIC PEROVSKITE FORMULATIONS

(71) Applicant: OXFORD PHOTOVOLTAICS LIMITED, Oxford, Oxfordshire (GB)

(72) Inventors: Nicola Beaumont, Oxford (GB); Brett Akira Kamino, Oxford (GB); Benjamin Langley, Oxford (GB); Edward James William Crossland, Oxford (GB)

(73) Assignee: OXFORD PHOTOVOLTAICS LIMITED, Oxford (GB)

( * ) Notice: Subject to any disclaimer, the term of this patent is extended or adjusted under 35 U.S.C. 154(b) by 363 days.

(21) Appl. No.: 15/509,990

(22) PCT Filed: Sep. 2, 2015

(86) PCT No.: PCT/GB2015/052535
§ 371 (c)(1),
(2) Date: Mar. 9, 2017

(87) PCT Pub. No.: WO2016/038338
PCT Pub. Date: Mar. 17, 2016

(65) Prior Publication Data
US 2017/0243699 A1 Aug. 24, 2017

(30) Foreign Application Priority Data
Sep. 10, 2014 (GB) .................. 1416042.8

(51) Int. Cl.
*C30B 29/54* (2006.01)
*H01G 9/20* (2006.01)
(Continued)

(52) U.S. Cl.
CPC ......... *H01G 9/2009* (2013.01); *C01G 21/006* (2013.01); *C07C 251/30* (2013.01); *H01G 9/2031* (2013.01); *H01L 31/032* (2013.01); *H01L 51/0032* (2013.01); *H01L 51/0077* (2013.01); *H01L 51/4226* (2013.01); *C01P 2002/34* (2013.01); *C01P 2002/72* (2013.01);
(Continued)

(58) Field of Classification Search
CPC ............ C30B 29/24; C30B 29/54; C30B 7/00
See application file for complete search history.

(56) References Cited

U.S. PATENT DOCUMENTS

| | | | |
|---|---|---|---|
| 2013/0233377 A1 | 9/2013 | Kanatzidis et al. | |
| 2016/0005547 A1* | 1/2016 | Seok ................... | H01L 51/4226 136/255 |
| 2016/0322591 A1* | 11/2016 | Seok ................... | H01L 51/0003 |

OTHER PUBLICATIONS

Dou, S. Y., et al. "Preparation and performance of organic-inorganic halide perovskites." Journal of Materials Science: Materials in Electronics 24.12 (2013): 4862-4867.
(Continued)

*Primary Examiner* — Robert M Kunemund
(74) *Attorney, Agent, or Firm* — Meunier Carlin & Curfman LLC

(57) ABSTRACT

A formulation for use in the preferential formation of thin films of a perovskite material AMX 3 with a certain required crystalline structure, wherein said formulation comprises two or more compounds which between them comprise one or more first organic cations A; one or more metalcations M; one or more second cations A'; one or more first anions X and one or more second anions X'.

16 Claims, 7 Drawing Sheets

(51) Int. Cl.
   H01L 51/42    (2006.01)
   C01G 21/00    (2006.01)
   H01L 51/00    (2006.01)
   C07C 251/30   (2006.01)
   H01L 31/032   (2006.01)
   H01L 31/0256  (2006.01)

(52) U.S. Cl.
   CPC .. C01P 2006/90 (2013.01); H01L 2031/0344 (2013.01); Y02E 10/549 (2013.01); Y02P 70/521 (2015.11)

(56) References Cited

OTHER PUBLICATIONS

Eperon, Giles E., et al. "Morphological control for high performance, solution-processed planar heterojunction perovskite solar cells." Advanced Functional Materials 24.1 (2014): 151-157.

Hao, Feng, et al. "Anomalous band gap behavior in mixed Sn and Pb perovskites enables broadening of absorption spectrum in solar cells." Journal of the American Chemical Society 136.22 (2014): 8094-8099.

Hao, Feng, et al. "Lead-free solid-state organic-inorganic halide perovskite solar cells." Nature Photonics 8.6 (2014): 489-494.

International Search Report and Written Opinion of the International Searching Authority, Application No. PCT/GB2015/052535, dated Nov. 3, 2015, 14 pages.

Lee, Yongjae, et al. "Pressure-induced phase transitions and templating effect in three-dimensional organic-inorganic hybrid perovskites." Physical Review B 68.2 (2003): 020103.

Mitzi, D. B., and K. Liang. "Synthesis, Resistivity, and Thermal Properties of the Cubic Perovskite NH2CH=NH2SnI3 and Related Systems." Journal of Solid State Chemistry 134.2 (1997): 376-381.

Ogomi, Yuhei, et al. "All-solid Sn/Pb halide perovskite sensitized solar cells." Photovoltaic Specialist Conference (PVSC), 2014 IEEE 40th. IEEE, 2014.

Pellet, Norman, et al. "Mixed-organic-cation Perovskite photovoltaics for enhanced solar-light harvesting." Angewandte Chemie International Edition 53.12 (2014): 3151-3157.

Search and Examination Report under Sections 17 and 18(3), Intellectual Property Office of the United Kingdom, Application No. GB1416042.8, dated Mar. 3, 2015, 6 pages.

Green, et al. "Solar cell efficiency tables (version 44)." Prog. Photovolt. Res. Appl. 2014; 22:701-710.

Rouquerol, J. et al. "Recommendations for the Characterization of Porous Solids." Pure & Appl. Chem., vol. 66, No. 8, pp. 1739-1758(1994).

Haber, J. "Manual on Catalyst Characterization (Recommendations 1991)." Pure & Appl. Chem., vol. 63, No. 9, pp. 1227-1246 (1991).

Kojima, Akihiro, et al. "Organometal halide perovskites as visible-light sensitizers for photovoltaic cells." Journal of the American Chemical Society 131.17 (2009): 6050-6051.

Eperon, Giles E., et al. "Formamidinium lead trihalide: a broadly tunable perovskite for efficient planar heterojunction solar cells." Energy & Environmental Science 7.3 (2014): 982-988.

* cited by examiner

MIXED ORGANIC-INORGANIC PEROVSKITE FORMULATIONS

FIELD OF THE INVENTION

The present invention relates to a formulation suitable for making hybrid organic-inorganic perovskite compounds which have a particular preferred crystalline structure, and to a process for obtaining such hybrid organic-inorganic perovskites. The invention also relates to optoelectronic devices including photovoltaic devices such as solar cells and light-emitting devices, which use the formulation of the invention for making hybrid organic-inorganic perovskite compounds with a particular preferred crystalline structure.

BACKGROUND OF THE INVENTION

Over the past forty years or so there has been an increasing realisation of the need to replace fossil fuels with more secure sustainable energy sources. The new energy supply must also have low environmental impact, be highly efficient and be easy to use and cost effective to produce. To this end, solar energy is seen as one of the most promising technologies, nevertheless, the high cost of manufacturing devices that capture solar energy, including high material costs, has historically hindered its widespread use.

Every solid has its own characteristic energy-band structure which determines a wide range of electrical characteristics. Electrons are able to transition from one energy band to another, but each transition requires a specific minimum energy and the amount of energy required will be different for different materials. The electrons acquire the energy needed for the transition by absorbing either a phonon (heat) or a photon (light). The term "band gap" refers to the energy difference range in a solid where no electron states can exist, and generally means the energy difference (in electron volts) between the top of the valence band and the bottom of the conduction band. The efficiency of a material used in a solar cell under normal sunlight conditions is a function of the band gap for that material. If the band gap is too high, most daylight photons cannot be absorbed; if it is too low, then most photons have much more energy than necessary to excite electrons across the band gap, and the rest will be wasted. The Shockley-Queisser limit refers to the theoretical maximum amount of electrical energy that can be extracted per photon of incoming light and is about 1.34 eV. The focus of much of the recent solar cell work has been the quest for materials which have a band gap as close as possible to this maximum.

One class of photovoltaic materials that has attracted significant interest has been the hybrid organic-inorganic halide perovskites. Materials of this type form an $ABX_3$ crystal structure which has been found to show a favourable band gap, a high absorption coefficient and long diffusion lengths, making such compounds ideal as an absorber in photovoltaic devices. Early examples of hybrid organic-inorganic metal halide perovskite materials are reported by Kojima, A., et al, Organometal Halide Perovskites as Visible Light Sensitizers for Photovoltaic Cells. *J. Am. Chem. Soc.* 131(17), 6050-6051 (2009) and are based on methyl ammonium (MA) lead halide perovskites ($CH_3NH_3PbI_3$ and $CH_3NH_3PbBr_3$); the $CH_3NH_3PbI_3$ material has a band gap of around 1.55 eV and addition of the bromine perovskites will typically shift the band gap to larger values. Kojima et al report that a solar energy conversion efficiency (or power energy conversion efficiency, PCE) of 3.8% can be obtained for the iodide material.

Further work described in US2013/0233377A1, details the preparation of A/M/X compounds, in which A is selected from organic cations and elements from group 1 of the periodic table, M is selected from at least groups 3, 4, 5, 13, 14 or 15 of the periodic table and X is selected from elements from groups 17 of the periodic table. Particular examples have the formula $AMI_3$ where A is methylammonium ($CH_3NH_3^+$), formamidinium ($HC(NH_2)_2^+$), methylformamidinium ($H_3CC(NH_2)_2^+$) or guanidinium ($C(NH_2)_3^+$).

More recently in 2014, work has been conducted on formamidinium lead iodide perovskite, $HC(NH_2)_2PbI_3$, not least because compared with the MA counterpart, formamidinium (FA) metal halide perovskite materials typically measures a narrower band gap of about 1.48 eV and hence is closer to the Shockley-Queisser limit (1.34 eV) which governs optimum solar conversion efficiency for a single junction device. Indeed, power conversion efficiencies (PCEs) of FA perovskites is reported to be over 17% (M. A. Green, K. Emery, Y. Hishikawa, W. Warta and E. D. Dunlop, Prog. Photovolt. Res. Appl., 2014, 22, 701), thus providing persuasive evidence that this type of perovskite material has the potential to provide excellent photovoltaic materials. Further factors in favour of FA/Pb/halide perovskites are that they demonstrate greater thermal and moisture stability compared to the MA counterparts.

However, in common with other organic-inorganic perovskites, FA metal halide perovskites are able to exist in different crystalline structures i.e. different phases; each is stable over a different range of temperatures and only one phase exhibits suitable electronic properties. Unfortunately, the formation of these different phases becomes a significant problem to the ability to the use of these compounds when the temperature range over which the material transitions from one phase to another, is low, for example below 200° C.

The two phases of FA/metal/halide perovskite materials as shown in the crystallographic schematic diagram of FIG. 1 are:
a) Alpha, perovskite-type trigonal (P3m1) a=8.9920, c=11.0139 Å polymorph. Stable phase at temperature (T)>60° C. (black); and
b) Delta, hexagonal-type ($P6_3mc$). Wide bandgap semiconductor but chain-like structure hinders electronic transport. Stable phase at temperature (T)<50° C. (yellow).

In the case of FA/metal/halide perovskite materials it is the black alpha phase which exhibits the suitable optical and electronic properties, thus it is desirable to prepare this phase in preference to the yellow delta phase. As a further difficulty, although phase transitions as a result of changing temperature are observed in the bulk powder materials, the same is not readily observed when the materials are formed in a thin film. In this case, the initial phase formed determines the prevailing phase, therefore it is very important to form the correct phase initially when making thin films of these materials. Another consideration is the importance of the kinetics of crystal formation being able to encourage or prevent the creation of phases that are not thermodynamically the most stable. For example, if one considers crystal formation as two steps, nucleation and then growth, it is possible to seed the nucleation of one phase in preference to the other. In thin film formation the surface on which the film is forming can play a role in seeding one phase over another.

The method used to make the perovskite material is found to have a profound effect on which crystalline phase is formed. As described, for example in G E. Eperon et al, Energy Environ. Sci. 2014, conventional formamidinium (FA) perovskites (FAPbI$_3$) can be formed in a one-step deposition process using a 1:1 stoichiometric precursor solution of lead iodide (PbI$_2$): formamidinium iodide (FAI) in N,N-dimethylformamide (DMF). This one-step deposition process which is followed by a thermal cure, can be performed under either ambient or inert conditions, but in neither environment is free of problems and both cause difficulty when trying selectively to prepare the alpha-phase perovskite. Firstly, under ambient conditions the one-step process favours the delta-phase, whereas a mixture of both the alpha- and delta-phases is formed when these conditions are used to make solution processed thin films. Another problem is that the delta-phase is the prominant material when the thin film product is formed on a meso-porous scaffold (e.g. zirconia or alumina structures). A yet further problem with the one-step process is that the starting materials poorly convert to the perovskite and this results in the presence of PbI$_2$ as an impurity in the product. Unfortunately, increasing the FAI content only leads to poor formation and poor performance of the thin film due to the presence of unreacted FAI, and this material presents another difficulty in that it cannot be easily removed owing to its low volatility.

Although using the one-step process under inert atmospheres is more likely to form the alpha-phase when forming thin films, as above the use of mesoporous scaffolds, such as alumina, again preferentially causes the formation of the delta-phase.

In an alternative process, for example as described in Pellet et al *Angew. Chemie* 2014, Vol. 53, Issue 12, pp 3151-3157, FAPbI$_3$ can be formed via a two-step deposition of PbI$_2$ with subsequent immersion in the FAI halide salt solution in iso-propyl alcohol (IPA). Typically, the procedure is conducted under inert and/or dry atmospheric conditions and is followed by thermal curing. This two-step process not only has the disadvantage that it requires more than one step which increases the complexity and cost of the process, but it leads to a mixture of the alpha- and delta-phases. Also, it can lead to poor conversion of the starting materials to the perovskite leaving unconverted PbI$_2$ within the film which along with the delta-phase will typically decrease charge transport capabilities, as well as useful spectral absorption, and therefore will exhibit poorer cell performance.

SUMMARY OF THE PRESENT INVENTION

The present invention seeks to devise a way to enable the preferential formation of a particular selected crystal phase of a perovskite material, either by preventing or encouraging formation of a thermodynamically favourable phase. In this regard, the selected crystal phase is that which has suitable optical and electronic properties for optoelectronic applications, which will typically be the crystalline phase/polymorph of the perovskite material that has a band gap below 3.0 eV. This preferred crystal phase is often substantially black in colour. In contrast, the crystal phase/polymorph of a perovskite material that is substantially yellow in colour usually has a bang gap of 3.0 eV or above.

Advantageously, substantially all of the starting materials will be consumed or eliminated in the production of the final perovskite with the particular selected phase, that is, substantially no unreacted starting materials will contaminate the final perovskite product. It is desirable that the by-products that will form are able to be removed using conditions that do not degrade final perovskite product. It will of further benefit that the present invention is straightforward and cost effective to perform.

In particular, the present invention aims to provide a new precursor solution preferably for use in a one step solution deposition process, which will show the following novel features:

1. Preferential formation (ideally >90%, further ideally >95% and extremely ideally 99%) of a required crystalline phase, desirably both in flat films and in meso-porous scaffolds.
2. Complete conversion or elimination of precursors (no starting material impurities).
3. Compatible with continuous and non-continuous (ST) photoactive layers.
4. Allow the use of ambient reaction conditions for example be able to be used in conditions of around 40% humidity.

Therefore, the present invention provides a formulation for use in the formation of thin films of a perovskite material of general formula AMX$_3$, wherein said formulation comprises two or more compounds which between them comprise one or more first cations, A; one or more metal cations, M; one or more first anions X, one or more second cations A'; and one or more second anions X'; and further wherein the amount of and choice of the one or more second cations A' and one or more second anions X' is selected to form one or more A'X'-containing compounds which are able to be fully or substantially fully separated from the AMX$_3$ material at a temperature which maintains the required crystalline structure of the hybrid perovskite material, and in which the A' and X' ions are predominantly ionically bonded. The temperature which maintains the required crystalline structure of the material is a temperature that does not degrade the perovskite material. Consequently, the temperature which maintains the required crystalline structure of the material is typically less than 200° C., and is preferably between 60° C. and 200° C.

Any ratio of ions may be selected which produces the required perovskite and satisfies the conditions for the A'X'-containing compounds. Convenient ratios of A:M:X are 0.5 to 2.5:0.5 to 2.5:3.5 to 6.5, alternatively 1.1 to 2.5:0.5 to 1.5:3.5 to 4.5 and further alternatively 1:1:3.

The required crystalline phase which will preferentially be formed using the formulation of the present invention will be the phase which exhibits favourable electronic properties; notably this will be the phase which corresponds with the most appropriate band gap. Consequently, the required crystalline structure of the material has a band gap below 3.0 eV, and preferably has a band gap from 1.5 eV to 2.3 eV. This preferred crystalline phase/polymorph is typically substantially black in colour. Advantageously, the formulation of the present invention will designed so as to preferentially form the desired crystalline phase even though this phase is not the most kinetically favourable.

The exact mechanism by which the formulation of the present invention produces the preferential crystalline phase is currently unknown, however the presence of the one or more second cations A' and the one or more second anions X' are believed to be critical components. For the avoidance of doubt, in all cases, the selection of second cations A' will not be identical to the selection of first cations A. The selection of first anions, X however, may or may not be identical to the selection of second anions, X'.

Not wishing to be bound by any particular theory, it is possible that the size of the A' and X' ions relative to the spacing between the atoms in the crystal lattice of the hybrid organic-inorganic perovskite, may be influential in choosing appropriate compounds to supply the A' and X' ions. Alternatively, the presence of the A' and X' may somehow hinder the crystallisation of the perovskite material in the phase which has the higher band gap, or conversely in some way encourage the crystallisation of the perovskite material in the phase which has the smaller band gap (i.e. below 3.0 eV). Thus, in the formulation of the present invention, the one or more second anions, A' and/or the one or more second anions, X' can interact with the nucleation and/or growth of the perovskite crystals to preferentially favour the formation of the particular chosen phase structure.

Despite not knowing the exact mechanism, it has been found that it is necessary for the amount of and choice of the one or more ions A' and X' to be selected so as to form one or more A'X'-containing compounds which are sufficiently volatile to be able to be fully or substantially fully separated from the $AMX_3$ material at a temperature which maintains the required crystalline structure of the hybrid organic-inorganic perovskite material. Highly preferably, the one or more second cations A' and the one or more second anions X' are selected such that they are able to form one or more A'X'-containing compounds which sublime or evaporate at a temperature which maintains the required crystalline structure of the perovskite material. In this regard, the temperature which maintains the required crystalline structure of the material is a temperature that does not degrade the perovskite material, which is typically a temperature of less than 200° C., and preferably a temperature between 60° C. and 200° C.

It is also believed to be important that the A'X'-containing compounds are predominantly ionically as opposed to covalently bonded. Moreover, it is highly likely that the A' and X' ions will take on at least one of a number of roles within the reaction process: for example, the ions A'/X' may compete kinetically with the other ions in the formulation to form a particular crystal structure in preference to another; the resulting crystal structure may then seed the perovskite material and, as a result of the particular structure adopted as a result of the A'/X' ions, encourage the perovskite to crystallise in a particular orientation. Another possibility is that the A' and X' ions interact with either the film and/or the substrate for example at the interface where the film and the support meet; this interaction may again encourage the perovskite to crystallise in a particular orientation. The relative size of the A' and X' ions may also produce stearic effects on the interaction of the ions in the formulation; this could also have a bearing on the kinetics of the interaction between the ions in the formulation.

In a preferred formulation of the present invention the one or more first cations A and/or the one or more second cations A', may comprise a cation with formula $(R_1R_2R_3R_4N)^+$, wherein each one of $R_1$, $R_2$, $R_3$ and $R_4$ is independently selected from hydrogen, unsubstituted or substituted $C_1$-$C_{20}$ alkyl or substituted or unsubstituted aryl. Further preferably each one of $R_1$, $R_2$, $R_3$ and $R_4$ is independently selected from hydrogen, unsubstituted or substituted $C_1$-$C_{10}$ alkyl or substituted or unsubstituted aryl.

In particularly suitable formulations according to the present invention at least one of the one or more first cations A, and/or at least one of the one or more second cations A', are selected from an anion which can include, but not limited to, ammonium ($NH_4^+$), methyl ammonium ($CH_3NH_3^+$), formamidinium ($HC(NH_2)_2^+$), methylformamidinium ($H_3CC(NH_2)_2^+$), guanidinium ($C(NH_2)_3^+$), tetramethylammonium ($(CH_3)_4N^+$), dimethylammonium ($(CH_3)_2NH_2^+$) and trimethylammonium ($(CH_3)_3NH^+$).

In another formulation according to the present invention, at least one of the one or more first cations A, and/or at least one of the one or more second cations A', may comprise one or more alkali metals, for example lithium (Li), sodium (Na), Potassium (K), rubidium (Rb), caesium (Cs), and francium (Fr).

Ideally, the one or more metal cations M in the formulation according to the invention are selected from group 2, groups 7 to 12 and groups 14 and 15 of the periodic table, ytterbium and europium. Divalent metals are particularly suitable. The one or more metal ions are preferably selected from one or more of lead, tin and bismuth. Metal halides are a particularly valuable source of metal ions.

Highly preferred formulations according to the present invention comprise two or more compounds which between them comprise formamidinium-containing cations, A; one or more metals, M, selected from Groups 14 and 15 of the periodic table; one or more first anions, X; methylammonium-containing cations, A' and one or more second anions, X'.

The one or more first anions X used in the formulation of the invention comprise one or more selected from halides, pseudohalides, chalcogenides and an anion of formula $RCOO^-$, wherein R is H or unsubstituted $C_{1-6}$ alkyl anions, wherein pseudohalides can include cyanides, cyanates, isocyanates, thiocyanates, isothiocyanates, etc. and azides and chalcogenides include an anion of an element from group 6. The term "chalcogenide", used herein, refers to a compound comprising at least one of a sulphide, selenide or telluride ion (i.e. $S^{2-}$, $Se^{2-}$, or $Te^{2-}$) Advantageously the first anions X comprise one or more halides.

Further advantageously, the one or more second anions X' comprise one or more selected from halides pseudohalides, chalcogenides and an anion of formula RCOO—, wherein R is H or unsubstituted C1-6 alkyl anions, wherein pseudohalides can include Cyanides, cyanates, isocyanates, thiocyanates, isothiocyanates, etc. and azides and chalcogenides include an anion of an element from group 6. Preferably, at least one of the second anions X', is different from the one or more halides, pseudohalides, chalcogenides and an anion of formula RCOO—, wherein R is H or unsubstituted C1-6 alkyl anions of the one or more first anions X.

The solubility of the precursor components in the solvent system is an important consideration when deciding which compounds to use to supply the A, M, X, A' and X' ions. Thus it may be advantageous to introduce the individual ions required for the $AMX_3$ material via compounds that are more soluble but containing ions not required for the $AMX_3$. For example, $PbCl_2$ may be preferred over $PbI_2$ because it is more soluble.

Particular advantageous formulations of the present invention comprise formamidinium cations and/or a methylammonium cations, and/or one or more metal ions and a first anion, X and a second anion, X'. At least one of X and X' is one or more halide anions selected from iodide, bromide, chloride and fluoride. Preferably, the selection of halides chosen for first anion X is not be the same as that chosen for alternative anion X'.

In a second aspect, the present invention provides a process for preparing thin films of a perovskite material of the general formula $AMX_3$ which has a required crystalline structure, comprising the steps:
  i) forming a precursor solution comprising a formulation according to any of claims 1 to 13, and a suitable carrier system; and
  ii) subjecting the precursor solution to a regime that facilitates a) the removal of the carrier solvent system, b) a curing process for the formation of the perovskite material and c) the full or substantially full removal reaction product between the one or more second cations A' and the one or more second anions X', under temperature and pressure conditions which maintain the required crystalline structure of the perovskite material.

A suitable carrier system can include a single or a mixture of solvents, such as one or more of dimethylformamide, dimethylsolfoxide and butyrolactone. Favourable solvents have a boiling point below about 220° C., particularly preferably below 190° C.

Preferably, step ii) in the process according to the invention involves heating the precursor solution using suitable temperature and pressure conditions to facilitate a) the removal of the carrier solvent system, b) the formation of the perovskite material and c) the full or substantially full removal of the one or more reaction products between the one or more second cations A' and the one or more second anions X'. The temperature and pressure conditions are selected so as to maintain the required crystalline structure of the perovskite material.

It is highly convenient if step ii) involves the full or substantially full removal of the reaction product between the one or more second cations A' and the one or more second anions X' from the precursor solution, by evaporation/sublimation at a temperature which maintains the required structure of the perovskite material. It is also of benefit that the A'X' compound is more volatile and hence preferentially removed over any other compound formed by the ions in the precursor solution.

In a preferred process, thin films of a hybrid organic-inorganic perovskite material of the formula $HC(NH_2)_2(M)X_{3-x}X'_x$ wherein M is a metal, and X and X' are each one or more halides, having an alpha-phase crystalline structure, are selectively prepared, by the steps:

i) forming a precursor solution comprising formamidinium cations, methylammonium cations, one or more metals (M) selected from Groups 14 and 15 of the periodic table and a suitable solvent, and two or more halide anions; and ii) subjecting the precursor solution to a regime that facilitates a) the removal of the carrier solvent system, b) a curing process for the formation of the hybrid organic-inorganic perovskite material with the required alpha-phase structure and c) the full or substantially full removal of the reaction product between the one or more second cations A' and the one or more second anions X' under temperature and pressure conditions which maintain the alpha-phase crystalline structure of the hybrid organic-inorganic perovskite material.

In a third aspect, the present invention provides a precursor solution for use to make a perovskite material, said precursor solution comprising a suitable solvent system and two or more compounds which between them comprise one or more first cations, A; one or more metals, M; one or more first anions, X; one or more second cations A'; and one or more second anions X'; and further wherein the ratio of ions is selected such that A:M:X is 1:1:3, and the amount of and choice of the one or more ions A' and X' is selected to form one or more A'X'-containing compounds which are able to be fully or substantially fully separated from the $AMX_3$ material at a temperature which maintains the required crystalline structure of the perovskite material.

In a fourth aspect, the present invention provides a formulation for use in the formation of a light absorbing perovskite material having a general formula of $AMX_3$, wherein A is one or more monovalent cations, M is one or more divalent metal cations, and X is one or more halide anions. The formulation comprises two or more compounds which between them comprise the one or more monovalent cations, A; the one or more divalent metal cations, M; the one or more halide anions, X; one or more further monovalent cations A'; and one or more further halide anions X'. The one or more further monovalent cations A' and the one or more further halide anions X' are selected to form one or more A'X'-containing compounds which are able to be fully or substantially fully separated from the $AMX_3$ material at a temperature which maintains the required crystalline structure of the material.

The temperature which maintains the required crystalline structure of the material is a preferably temperature that does not degrade the perovskite material. Preferably, the temperature which maintains the required crystalline structure of the material is less than 200° C., and is preferably between 60° C. and 200° C.

The required crystalline structure is a crystalline phase/polymorph that is preferably substantially black in colour. The required crystalline structure of the material typically has a band gap below 3.0 eV, and preferably has a band gap from 1.5 eV to 2.3 eV.

The formulation may comprise an excess of the one or more further monovalent cations A' and the one or more further halide anions X'. The ratio of the one or more further monovalent cations A' and the one or more further halide anions X to the one or more monovalent cations, A, and the one or more halide anions, X, may be from 1.6:1 to 2.1:1, and is preferably from 1.2:1 and 2:1.

The one or more further monovalent cations A' and the one or more further halide anions X' are preferably selected to form one or more A'X'-containing compounds which are able to be fully or substantially fully separated from the $AMX_3$ material at a temperature of less than 200° C.

In the formulation, A may be one or two monovalent cations, M may be a divalent metal cation, and X may be one or more halide anions. The formulation then comprises two or more compounds which between them comprise the one or two monovalent cations, A; the divalent metal cation, M; the one or more halide anions, X; a further monovalent cation A'; and a further halide anion X'.

A may comprise, or may optionally consist of, a first monovalent cation. The formulation then comprises a first precursor compound comprising the first monovalent cation, A, and a halide anion, X; a second precursor compound comprising a further monovalent cation, A', and a halide anion, X; and a third precursor compound comprising a metal cation, M, and a further halide anion, X'.

A may comprise, or may optionally consist of, a first monovalent cation, $A_1$, and a second monovalent cation, $A_2$. The formulation then comprises a first precursor compound comprising the first monovalent cation, $A_1$, and a halide anion, X; a second precursor compound comprising a further monovalent cation, A', and a halide anion, X; a third precursor compound comprising the second monovalent cation, $A_2$, and a halide anion, X; and a fourth precursor compound comprising a metal cation, M, and a further halide anion, X'.

In the formulation, at least one of the one or more monovalent cations, A, and the one or more further monovalent cations, A', may be selected from ammonium ($NH_4^+$), methyl ammonium ($CH_3NH_3^+$), formamidinium ($HC(NH_2)_2^+$), methylformamidinium ($H_3CC(NH_2)_2^+$), guanidinium ($C(NH_2)_3^+$), tetramethylammonium $((CH_3)_4N^+)$, dimethylammonium $((CH_3)_2NH_2^+)$ and trimethylammonium $((CH_3)_3NH^+)$, $Cs^+$, $Rb^+$, $Cu^+$, $Pd^+$, $Pt^+$, $Ag^+$, $Au^+$, $Rh^+$, and $Ru^+$.

In the formulation, A may be one or more monovalent cations selected from methyl ammonium $(CH_3NH_3^+)$, formamidinium $(HC(NH_2)_2^+)$, ethyl ammonium $(CH_3CH_2NH_3^+)$, $Cs^+$, $Rb^+$, $Cu^+$, $Pd^+$, $Pt^+$, $Ag^+$, $Au^+$, $Rh^+$, and $Ru^+$, and preferably A is one or more monovalent cations selected from methyl ammonium $(CH_3NH_3^+)$, formamidinium $(HC(NH_2)_2^+)$, and $Cs^+$. In the formulation, A may comprises any of methyl ammonium $(CH_3NH_3^+)$ and formamidinium $(HC(NH_2)_2^+)$; formamidinium $(HC(NH_2)_2^+)$ and $Cs^+$; and formamidinium $(HC(NH_2)_2^+)$.

In the formulation, A' may comprise any of ammonium $(NH_4^+)$, methyl ammonium $(CH_3NH_3^+)$, and preferably A' comprises methyl ammonium $(CH_3NH_3^+)$. M may comprise one or more of $Pb^{2+}$, $Sn^{2+}$, and $Bi^{2+}$, is preferably selected from $Pb^{2+}$ and $Sn^{2+}$, and is more preferably $Pb^{2+}$.

X may comprise one or more halide anions selected from fluoride, chloride, bromide, and iodide, and preferably selected from chloride, bromide and iodide, and more preferably selected from bromide and iodide. X' may comprise one or more halide anions selected from fluoride, chloride, bromide, and iodide, and preferably selected from chloride, bromide and iodide, and more preferably chloride.

In a fifth aspect, the present invention provides precursor solution for use in the formation of a light absorbing perovskite material having a general formula of $AMX_3$, wherein A is one or more monovalent cations, M is one or more divalent metal cations, and X is one or more halide anions, the precursor solution comprising the formulation according to the fourth aspect dissolved in a suitable solvent system. The solvent system may comprise one or more solvents selected from dimethyl sulfoxide (DMSO), N,N-dimethylformamide (DMF), N-cyclohexyl-2-pyrrolidone (CHP), and dimethylacetamide (DMAc).

In a sixth aspect, the present invention provides method of producing a photovoltaic device comprising a photoactive material, which photoactive material comprises a perovskite of general formula $AMX_3$, wherein A is one or more monovalent cations, M is one or more divalent metal cations, and X is one or more halide anions. The method comprises:
 forming a precursor solution by dissolving the formulation according to the fourth aspect in a solvent system;
 disposing/depositing a layer of the precursor solution; and
 removing the solvent system to produce a solid layer of the perovskite material.

The layer of the precursor solution may be disposed on a first region, the first region comprising any of an n-type region comprising at least one n-type layer; and a p-type region comprising at least one p-type layer.

The method may further comprise disposing a second region above the solid layer of the perovskite material. The first region may then comprise one of an n-type region comprising at least one n-type layer and a p-type region comprising at least one p-type layer, and the second region may comprise the other of the n-type region comprising at least one n-type layer and the p-type region comprising at least one p-type layer. Alternatively, the first region may comprise an n-type region comprising at least one n-type layer, and the second region may comprise an electrode and/or metal layer. In this arrangement, the electrode and/or metal layer of the second region is preferably in direct contact with the solid layer of the perovskite material.

The step of removing the solvent system may comprise heating the layer of the precursor solution to a temperature of less than 200° C., and preferably between 60° C. and 200° C.

BRIEF DESCRIPTION OF THE DRAWINGS

The present invention will now be described with reference to the following figures in which.

DETAILED DESCRIPTION

Definitions

Figure 1:
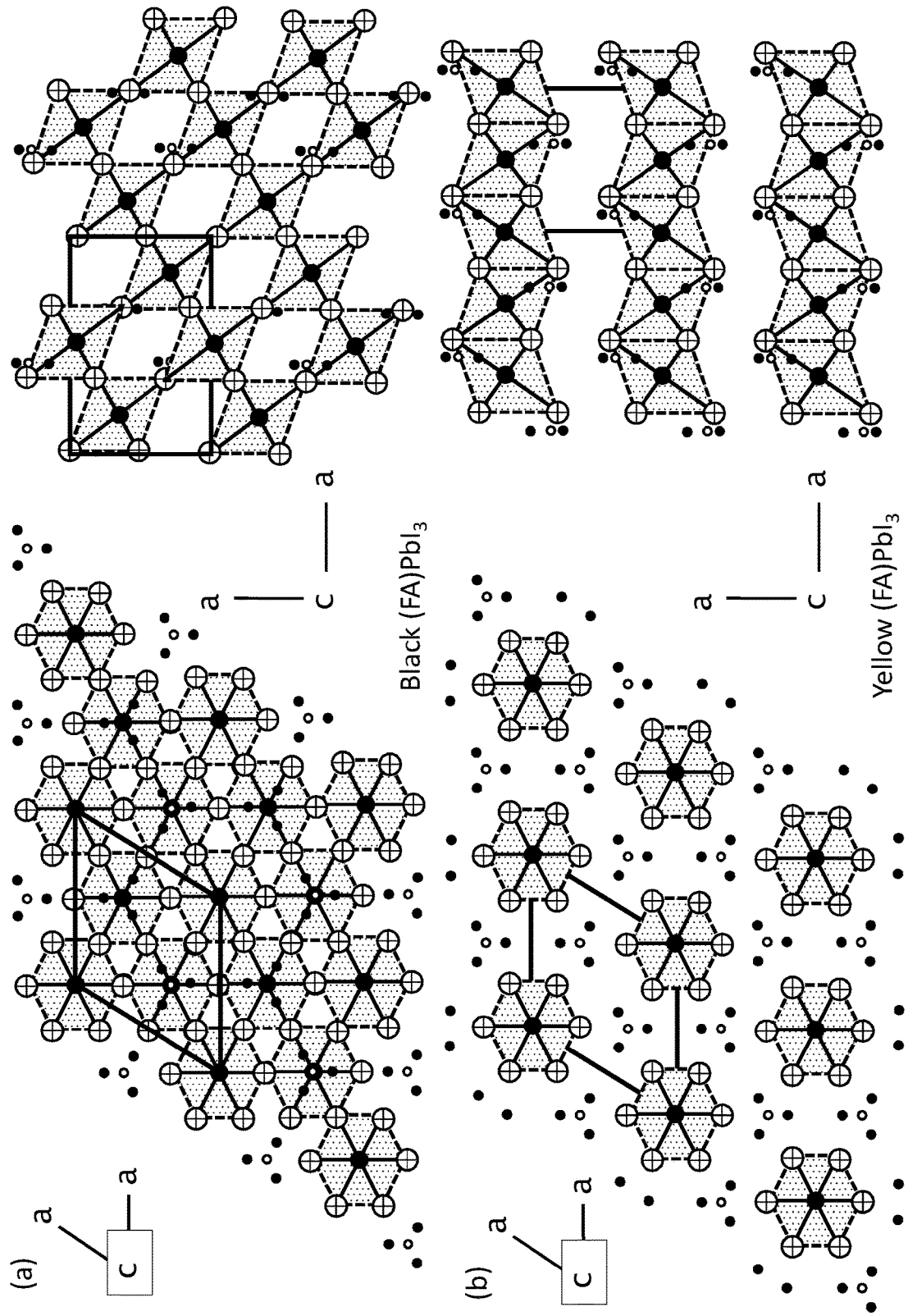
FIG. 1 is a crystallographic schematic diagram of the a) alpha and b) delta phases of formamidinium lead perovskite.

The term "photoactive", as used herein, refers to a region, layer or material that is capable of responding to light photoelectrically. A photoactive region, layer or material is therefore capable of absorbing the energy carried by photons in light that then results in the generation of electricity (e.g. by generating either electron-hole pairs or excitons).

The term "perovskite", as used herein, refers to a material with a three-dimensional crystal structure related to that of $CaTiO_3$ or a material comprising a layer of material, which layer has a structure related to that of $CaTiO_3$. The structure of $CaTiO_3$ can be represented by the formula $ABX_3$, wherein A and B are cations of different sizes and X is an anion. In the unit cell, the A cations are at (0,0,0), the B cations are at (1/2, 1/2, 1/2) and the X anions are at (1/2, 1/2, 0). The A cation is usually larger than the B cation. The skilled person will appreciate that when A, B and X are varied, the different ion sizes may cause the structure of the perovskite material to distort away from the structure adopted by $CaTiO_3$ to a lower-symmetry distorted structure. The symmetry will also be lower if the material comprises a layer that has a structure related to that of $CaTiO_3$. Materials comprising a layer of perovskite material are well known. For instance, the structure of materials adopting the $K_2NiF_4$ type structure comprises a layer of perovskite material. The skilled person will appreciate that a perovskite material can be represented by the formula [A][B][X]$_3$, wherein [A] is at least one cation, [B] is at least one cation and [X] is at least one anion. When the perovskite comprises more than one A cation, the different A cations may distributed over the A sites in an ordered or disordered way. When the perovskite comprises more than one B cation, the different B cations may distributed over the B sites in an ordered or disordered way. When the perovskite comprise more than one X anion, the different X anions may distributed over the X sites in an ordered or disordered way. The symmetry of a perovskite comprising more than one A cation, more than one B cation or more than one X cation, will often be lower than that of $CaTiO_3$.

As mentioned in the preceding paragraph, the term "perovskite", as used herein, refers to (a) a material with a three-dimensional crystal structure related to that of $CaTiO_3$ or (b) a material comprising a layer of material, wherein the layer has a structure related to that of $CaTiO_3$. Although both of these categories of perovskite may be used in the devices according to the invention, it is preferable in some circumstances to use a perovskite of the first category, (a), i.e. a perovskite having a three-dimensional (3D) crystal structure. Such perovskites typically comprise a 3D network of perovskite unit cells without any separation between layers. Perovskites of the second category, (b), on the other hand, include perovskites having a two-dimensional (2D) layered structure. Perovskites having a 2D layered structure may comprise layers of perovskite unit cells that are separated by (intercalated) molecules; an example of such a 2D layered perovskite is $[2-(1-cyclohexenyl)ethylammonium]_2PbBr_4$. 2D layered perovskites tend to have high exciton binding energies, which favours the generation of bound electron-hole pairs (excitons), rather than free charge carriers, under photoexcitation. The bound electron-hole pairs may not be sufficiently mobile to reach the p-type or n-type contact where they can then transfer (ionise) and generate free charge. Consequently, in order to generate free charge, the exciton binding energy has to be overcome, which represents an energetic cost to the charge generation process and results in a lower voltage in a photovoltaic cell and a lower efficiency. In contrast, perovskites having a 3D crystal structure tend to have much lower exciton binding energies (on the order of thermal energy) and can therefore generate free carriers directly following photoexcitation. Accordingly, the perovskite employed in the devices and processes of the invention is preferably a perovskite of the first category, (a), i.e. a perovskite which has a three-dimensional crystal structure. This is particularly preferable when the optoelectronic device is a photovoltaic device.

The perovskite material employed in the present invention is one which is capable of absorbing light and thereby generating free charge carriers. Thus, the perovskite employed is a light-absorbing perovskite material. However, the skilled person will appreciate that the perovskite material could also be a perovskite material that is capable of emitting light, by accepting charge, both electrons and holes, which subsequently recombine and emit light. Thus, the perovskite employed may be a light-emitting perovskite.

As the skilled person will appreciate, the perovskite material employed in the present invention may be a perovskite which acts as an n-type, electron-transporting semiconductor when photo-doped. Alternatively, it may be a perovskite which acts as a p-type hole-transporting semiconductor when photo-doped. Thus, the perovskite may be n-type or p-type, or it may be an intrinsic semiconductor. In preferred embodiments, the perovskite employed is one which acts as an n-type, electron-transporting semiconductor when photo-doped. The perovskite material may exhibit am bipolar charge transport, and therefore act as both n-type and p-type semiconductor. In particular, the perovskite may act as both n-type and p-type semiconductor depending upon the type of junction formed between the perovskite and an adjacent material.

Typically, the perovskite semiconductor used in the present invention is a photosensitizing material, i.e. a material which is capable of performing both photogeneration and charge transportation.

The term "organic" takes its normal meaning in the art. Typically, an organic material refers to a material comprising one or more compounds that comprise a carbon atom. As the skilled person would understand it, an organic compound may comprise a carbon atom covalently bonded to another carbon atom, or to a hydrogen atom, or to a halogen atom, or to a chalcogen atom (for instance an oxygen atom, a sulphur atom, a selenium atom, or a tellurium atom). The skilled person will understand that the term "organic compound" does not typically include compounds that are predominantly ionic such as carbides, for instance.

The term "organic cation" refers to a cation comprising carbon. The cation may comprise further elements, for example, the cation may comprise hydrogen, nitrogen or oxygen. The term "inorganic cation" refers to a cation that is not an organic cation. By default, the term "inorganic cation" refers to a cation that does not contain carbon.

The term "semiconductor", as used herein, refers to a material with electrical conductivity intermediate in magnitude between that of a conductor and a dielectric. A semiconductor may be an n-type semiconductor, a p-type semiconductor or an intrinsic semiconductor.

The term "dielectric", as used herein, refers to material which is an electrical insulator or a very poor conductor of electric current. The term dielectric therefore excludes semiconducting materials such as titania. The term dielectric, as used herein, typically refers to materials having a band gap of equal to or greater than 4.0 eV (The band gap of titania is about 3.2 eV.)

The term "n-type", as used herein, refers to a region, layer or material that comprises an extrinsic semiconductor with a larger concentration of electrons than holes. In n-type semiconductors, electrons are therefore majority carriers and holes are the minority carriers, and they are therefore electron transporting materials. The term "n-type region", as used herein, therefore refers to a region of one or more electron transporting (i.e. n-type) materials. Similarly, the term "n-type layer" refers to a layer of an electron-transporting (i.e. an n-type) material. An electron-transporting (i.e. an n-type) material could be a single electron-transporting compound or elemental material, or a mixture of two or more electron-transporting compounds or elemental materials. An electron-transporting compound or elemental material may be undoped or doped with one or more dopant elements.

The term "p-type", as used herein, refers to a region, layer or material that comprises an extrinsic semiconductor with a larger concentration of holes than electrons. In p-type semiconductors, holes are the majority carriers and electrons are the minority carriers, and they are therefore hole transporting materials. The term "p-type region", as used herein, therefore refers to a region of one or more hole transporting (i.e. p-type) materials. Similarly, the term "p-type layer" refers to a layer of a hole-transporting (i.e. a p-type) material. A hole-transporting (i.e. a p-type) material could be a single hole-transporting compound or elemental material, or a mixture of two or more hole-transporting compounds or elemental materials. A hole-transporting compound or elemental material may be undoped or doped with one or more dopant elements.

The term "band gap", as used herein, refers to the energy difference between the top of the valence band and the bottom of the conduction band in a material. The skilled person may readily measure the band gap of a material without undue experimentation.

The term "layer", as used herein, refers to any structure which is substantially laminar in form (for instance extending substantially in two perpendicular directions, but limited in its extension in the third perpendicular direction). A layer may have a thickness which varies over the extent of the layer. Typically, a layer has approximately constant thickness. The "thickness" of a layer, as used herein, refers to the average thickness of a layer. The thickness of layers may easily be measured, for instance by using microscopy, such as electron microscopy of a cross section of a film, or by surface profilometry for instance using a stylus profilometer.

The term "porous", as used herein, refers to a material within which pores are arranged. Thus, for instance, in a porous material the pores are volumes within the body of the material where there is no material. The individual pores may be the same size or different sizes. The size of the pores is defined as the "pore size". The limiting size of a pore, for most phenomena in which porous solids are involved, is that of its smallest dimension which, in the absence of any further precision, is referred to as the width of the pore (i.e. the width of a slit-shaped pore, the diameter of a cylindrical or spherical pore, etc.). To avoid a misleading change in scale when comparing cylindrical and slit-shaped pores, one should use the diameter of a cylindrical pore (rather than its length) as its "pore-width" (Rouquerol, J. et al, (1994) Recommendations for the characterization of porous solids (Technical Report). Pure and Applied Chemistry, 66(8)). The following distinctions and definitions were adopted in previous IUPAC documents (J. Haber. (1991) Manual on catalyst characterization (Recommendations 1991). Pure and Applied Chemistry.): micropores have widths (i.e. pore sizes) smaller than 2 nm; Mesopores have widths (i.e. pore sizes) of from 2 nm to 50 nm; and Macropores have widths (i.e. pore sizes) of greater than 50 nm. In addition, nanopores may be considered to have widths (i.e. pore sizes) of less than 1 nm.

Pores in a material may include "closed" pores as well as open pores. A closed pore is a pore in a material which is a non-connected cavity, i.e. a pore which is isolated within the material and not connected to any other pore and which cannot therefore be accessed by a fluid to which the material is exposed. An "open pore" on the other hand, would be accessible by such a fluid. The concepts of open and closed porosity are discussed in detail in J. Rouquerol et al.

Open porosity, therefore, refers to the fraction of the total volume of the porous material in which fluid flow could effectively take place. It therefore excludes closed pores. The term "open porosity" is interchangeable with the terms "connected porosity" and "effective porosity", and in the art is commonly reduced simply to "porosity". The term "without open porosity", as used herein, therefore refers to a material with no effective porosity. Thus, a material without open porosity typically has no macropores and no mesopores. A material without open porosity may comprise micropores and nanopores, however. Such micropores and nanopores are typically too small to have a negative effect on a material for which low porosity is desired.

In addition, polycrystalline materials are solids that are composed of a number of separate crystallites or grains, with grain boundaries at the interface between any two crystallites or grains in the material. A polycrystalline material can therefore have both interparticle/interstitial porosity and intraparticle/internal porosity. The terms "interparticle porosity" and "interstitial porosity", as used herein, refer to pores between the crystallites or grains of the polycrystalline material (i.e. the grain boundaries), whilst the terms "intraparticle porosity" and "internal porosity", as used herein, refer to pores within the individual crystallites or grains of the polycrystalline material. In contrast, a single crystal or monocrystalline material is a solid in which the crystal lattice is continuous and unbroken throughout the volume of the material, such that there are no grain boundaries and no interparticle/interstitial porosity.

The term "compact layer", as used herein, refers to a layer without mesoporosity or macroporosity. A compact layer may sometimes have microporosity or nanoporosity.

The term "scaffold material", as used herein, therefore refers to a material that is capable of acting as a support for a further material. The term "porous scaffold material", as used herein, therefore refers to a material which is itself porous, and which is capable of acting as a support for a further material.

The term "transparent", as used herein, refers to material or object allows visible light to pass through almost undisturbed so that objects behind can be distinctly seen. The term "semi-transparent", as used herein, therefore refers to material or object which has a transmission (alternatively and equivalently referred to as a transmittance) to visible light intermediate between a transparent material or object and an opaque material or object. Typically, a transparent material will have an average transmission for visible light (generally light with a wavelength of from 370 to 740 nm) of around 100%, or from 90 to 100%. Typically, an opaque material will have an average transmission for visible light of around 0%, or from 0 to 5%. A semi-transparent material or object will typically have an average transmission for visible light of from 10 to 90%, typically 40 to 60%. Unlike many translucent objects, semi-transparent objects do not typically distort or blur images. Transmission for light may be measured using routine methods, for instance by comparing the intensity of the incident light with the intensity of the transmitted light.

The term "electrode", as used herein, refers to a conductive material or object through which electric current enters or leaves an object, substance, or region. The term "negative electrode", as used herein, refers to an electrode through which electrons leave a material or object (i.e. an electron collecting electrode). A negative electrode is typically referred to as an "anode". The term "positive electrode", as used herein, refers to an electrode through which holes leave a material or object (i.e. a hole collecting electrode). A positive electrode is typically referred to as a "cathode". Within a photovoltaic device, electrons flow from the positive electrode/cathode to the negative electrode/anode, whilst holes flow from the negative electrode/anode to the positive electrode/cathode.

The term "charge transporter" refers to a region, layer or material through which a charge carrier (i.e. a particle carrying an electric charge), is free to move. In semiconductors, electrons act as mobile negative charge carriers and holes act as mobile positive charges. The term "electron transporter" therefore refers to a region, layer or material through which electrons can easily flow and that will typically reflect holes (a hole being the absence of an electron that is regarded as a mobile carrier of positive charge in a semiconductor). Conversely, the term "hole transporter" refers to a region, layer or material through which holes can easily flow and that will typically reflect electrons.

The term "consisting essentially of" refers to a composition comprising the components of which it consists essentially as well as other components, provided that the other components do not materially affect the essential characteristics of the composition. Typically, a composition consisting essentially of certain components will comprise greater than or equal to 95 wt % of those components or greater than or equal to 99 wt % of those components.

The term "volatile compound", as used herein, refers to a compound which is easily removed by evaporation or decomposition. For instance a compound which is easily removed by evaporation or decomposition at a temperature of less than or equal to 200° C. would be a volatile compound. "Volatile compound" also includes compounds which are easily removed by evaporation via decomposition products. Thus, a volatile compound X may evaporate easily thorough evaporation of molecules of X, or a volatile compound X may evaporate easily by decomposing to form two compounds Y and Z which evaporate easily. Thus, a volatile compound X may have a relatively high vapour pressure (e.g. greater than or equal to 500 Pa) or may have a relatively high decomposition pressure (e.g. greater than or equal to 500 Pa for one or more of the decomposition products), which may also be referred to as a dissociation pressure.

Formulation for Use in the Formation of the Perovskite Material

As noted above, the formulation of the present invention is for use in the formation of a light absorbing perovskite material having a general formula (I) of:

$$AMX_3 \tag{I}$$

wherein A is one or more monovalent cations, M is one or more divalent metal cations, and X is one or more halide anions. The formulation comprises two or more compounds which between them comprise:
the one or more monovalent cations, A;
the one or more divalent metal cations, M;
the one or more halide anions, X;
one or more further monovalent cations A'; and
one or more further halide anions X'.

The one or more further monovalent cations A' and the one or more further halide anions X' are selected to form one or more A'X'-containing compounds which are able to be fully or substantially fully separated from the $AMX_3$ material at a temperature which maintains the required crystalline structure of the material.

In this regard, the temperature which maintains the required crystalline structure of the material is a temperature that does not degrade the perovskite material. Preferably, the temperature which maintains the required crystalline structure of the material is less than 200° C., and is more preferably between 60° C. and 200° C. The one or more further monovalent cations A' and the one or more further halide anions X' are therefore preferably selected to form one or more A'X'-containing compounds which are able to be fully or substantially fully separated from the $AMX_3$ material at a temperature of less than 200° C.

The required crystalline structure is a crystalline phase/polymorph that is preferably substantially black in colour. The required crystalline structure of the material typically has a band gap below 3.0 eV, and preferably has a band gap from 1.5 eV to 2.3 eV.

The formulation may comprise an excess of the one or more further monovalent cations A' and the one or more further halide anions X'. The ratio of the one or more further monovalent cations A' and the one or more further halide anions X to the one or more monovalent cations A and the one or more halide anions X may be from 1.6:1 to 2.1:1, and is preferably from 1.2:1 and 2:1.

In the formulation, A may be one or two monovalent cations, M may be a divalent metal cation, and X may be one or more halide anions. The formulation then comprises two or more compounds which between them comprise the one or two monovalent cations A; the divalent metal cation M; the one or more halide anions X; a further monovalent cation A'; and a further halide anion X'.

In the formulation, A may comprise, or may optionally consist of, a first monovalent cation. The formulation then comprises a first precursor compound comprising the first monovalent cation A, and a halide anion X; a second precursor compound comprising a further monovalent cation A', and a halide anion X; and a third precursor compound comprising a metal cation M, and a further halide anion X'.

In the formulation, A may comprise, or may optionally consist of, a first monovalent cation $A_1$, and a second monovalent cation $A_2$. The formulation then comprises a first precursor compound comprising the first monovalent cation $A_1$, and a halide anion X; a second precursor compound comprising a further monovalent cation A', and a halide anion X; a third precursor compound comprising the second monovalent cation $A_2$, and a halide anion, X; and a fourth precursor compound comprising a metal cation M, and a further halide anion X'.

In the formulation, the one or more organic first A and/or the one or more second cations A' may comprise a cation with formula $(R_1R_2R_3R_4N)^+$, wherein each one of $R_1$, $R_2$, $R_3$ and $R_4$ is independently selected from hydrogen, unsubstituted or substituted $C_1$-$C_{20}$ alkyl or substituted or unsubstituted aryl.

In the formulation, at least one of the one or more monovalent cations A and the one or more further monovalent cations A' may be selected from ammonium ($NH_4^+$), methyl ammonium ($CH_3NH_3^+$), formamidinium ($HC(NH_2)_2^+$), methylformamidinium ($H_3CC(NH_2)_2^+$), guanidinium ($C(NH_2)_3^+$), tetramethylammonium (($CH_3)_4N^+$), dimethylammonium (($CH_3)_2NH_2^+$) and trimethylammonium (($CH_3)_3NH+$), $Cs^+$, $Rb^+$, $Cu^+$, $Pd^+$, $Pt^+$, $Ag^+$, $Au^+$, $Rh^+$, and $Ru^+$.

In the formulation, A may be one or more monovalent cations selected from methyl ammonium ($CH_3NH_3^+$), formamidinium ($HC(NH_2)_2^+$), ethyl ammonium ($CH_3CH_2NH_3^+$), $Cs^+$, $Rb^+$, $Cu^+$, $Pd^+$, $Pt^+$, $Ag^+$, $Au^+$, $Rh^+$, and $Ru^+$, and preferably A is one or more monovalent cations selected from methyl ammonium ($CH_3NH_3^+$), formamidinium ($HC(NH_2)_2^+$), and $Cs^+$. In preferred embodiments, A may comprise any of methyl ammonium ($CH_3NH_3^+$) and formamidinium ($HC(NH_2)_2^+$); formamidinium ($HC(NH_2)_2^+$) and $Cs^+$; and formamidinium ($HC(NH_2)_2^+$).

In the formulation, A' may comprise any of ammonium ($NH_4^+$), methyl ammonium ($CH_3NH_3^+$), and preferably A' comprises methyl ammonium ($CH_3NH_3^+$). M may comprise one or more of $Pb^{2+}$, $Sn^{2+}$, and $Bi^{2+}$, is preferably selected from $Pb^{2+}$ and $Sn^{2+}$, and is more preferably $Pb^{2+}$.

In the formulation, X may comprise one or more halide anions selected from fluoride, chloride, bromide, and iodide, and preferably selected from chloride, bromide and iodide, and more preferably selected from bromide and iodide. X' may comprise one or more halide anions selected from fluoride, chloride, bromide, and iodide, and preferably selected from chloride, bromide and iodide, and more preferably chloride. Preferably, the selection of halides chosen for first anion X will not be the same as that chosen for second anion X'.

In addition, a precursor solution for use in the formation of a light absorbing perovskite material having a general formula of (I) can be provided by dissolving the precursor compounds of the above described formulations in a suitable solvent system. The precursor solution therefore comprises a solution of the cations and anions that comprise each of the precursor compounds.

The suitable solvent system is chosen such that is able to solubilise all of the components of the formulation and/or is able to be readily removed from the perovskite material whilst maintaining its required crystalline structure. Typically, the solvent system may comprise one or more solvents selected from dimethyl sulfoxide (DMSO), N,N-dimethylformamide (DMF), N-cyclohexyl-2-pyrrolidone (CHP), and dimethylacetamide (DMAc).

Method of Producing a Photovoltaic Device

There is also provided a method of producing a photovoltaic device comprising a photoactive material, which photoactive material comprises a perovskite of general formula (I). The method comprises a step (a) of forming a precursor solution by dissolving the above-described formulation in a solvent system; a step (b) of disposing/depositing a layer of the precursor solution; and a step (c) of removing the solvent system to produce a solid layer of the perovskite material.

The layer of the precursor solution may be disposed on a first region, the first region comprising any of an n-type region comprising at least one n-type layer; and a p-type region comprising at least one p-type layer.

The method may further comprise disposing a second region above the solid layer of the perovskite material. The first region may then comprise one of an n-type region comprising at least one n-type layer and a p-type region comprising at least one p-type layer, and the second region may comprise the other of the n-type region comprising at least one n-type layer and the p-type region comprising at least one p-type layer. Alternatively, the first region may comprise an n-type region comprising at least one n-type layer, and the second region may comprise an electrode and/or metal layer. In this arrangement, the electrode and/or metal layer of the second region is preferably in direct contact with the solid layer of the perovskite material.

The step of removing the solvent system may comprise heating the layer of the precursor solution to a temperature of less than 200° C., and preferably between 60° C. and 200° C.

EXAMPLES

Materials.

In the exemplary embodiments detailed below, unless otherwise stated, all materials were purchased from Sigma-Aldrich or Alfa Aesar and used as received. Spiro-OMeTAD was purchased from Lumtec.

Perovskite precursor synthesis: Formamidinium iodide (FAI) were synthesised by dissolving formamidinium acetate powder in a 2× molar excess of 57% w/w hydroiodic acid (for FAI). After addition of acid the solution was left stirring for 10 minutes at 50° C. Upon drying at 100° C., a yellow-white powder is formed. This was then washed with diethyl ether and recrystallized twice with ethanol, to form white needle-like crystals. This was previously demonstrated by Eperon et al. Before use, it was dried overnight in a vacuum oven. The methylammonium iodide (MAI) was synthesised according to literature methods.

To form $FAPbI_3$ precursor solutions, FAI, MAI and $PbCl_2$ (or $PbI_2$) were dissolved in anhydrous N,N-dimethylformamide (DMF) or dimethylsulfoxide, (DMSO) in the various ratios as described in Table 1 below with the lead content always 0.88 M. Films were spin-coated at 2000 rpm and annealed at 150° C. for 30 mins (unless stated otherwise).

$MAPbI_3$ precursor was prepared by dissolving equimolar amounts of methylammonium iodide (synthesised according to literature procedures) and $PbI_2$ in DMF at 40 wt % total solids. Films were spin-coated at 2000 rpm and annealed at 100° C. for 50 minutes under ambient conditions.

Substrate Preparation: Devices were fabricated on fluorine-doped tin oxide (FTO) coated glass (Pilkington, 7 Ω $sq^{-1}$). Initially FTO was removed from regions under the anode contact by etching the FTO with 2M HCl and zinc powder. Substrates were then cleaned sequentially in hellmanex detergent, acetone, propan-2-ol and oxygen plasma. A ~40 nm hole-blocking layer of compact $TiO_2$ was deposited by spin-coating a mildly acidic solution of titanium isopropoxide in ethanol at 2000 rpm, and annealed at 500° C. for 30 minutes.

Perovskite Solar Cell Fabrication: To form the $FAPbI_3$ layer, the 0.88M precursor was spin-coated in ambient conditions at 2000 rpm. The films were then annealed in air at 150° C. for 30 minutes.

The hole-transporting layer was then deposited via spin-coating a 8.5 wt % solution in chlorobenzene of 2,2',7,7'-tetrakis-(N,N-di-p-methoxyphenylamine)9,9'-spirobifluorene (spiro-OMeTAD), with additives of lithium bis (trifluoromethanesulfonyl)imide (added in an acetonitrile solution) and 4-tert-butylpyridine. Spin-coating was carried out in air at 2000 rpm. Gold electrodes were thermally evaporated under vacuum of ~$10^{-6}$ Torr (~$133.32 \times 10^{-6}$ Pa), at a rate of ~0.1 $nms^{-1}$, to complete the devices.

Device characterisation: The current density-voltage (J-V) curves were measured (2400 Series SourceMeter, Keithley Instruments) under simulated AM 1.5 sunlight at 100 $mWcm^{-2}$ irradiance generated by an Abet Class AAB sun 2000 simulator, with the intensity calibrated with an NREL calibrated KG5 filtered Si reference cell.

Optical measurements: Absorbance spectra were collected with a Perkin Elmer 300 UV-Vis spectrophotometer with an internally coupled integrating sphere.

Materials Characterization: X-ray diffraction spectra were obtained from films deposited onto c-$TiO_2$/FTO using a Panalytical X'Pert Pro x-ray diffractometer.

Formulations and Film Formation

Table 1 is a summary of the formulations used to form $FAPbI_3$ perovskites. The formulations labelled OxPVF0, OxPVF1 and OxPVF2 are comparative examples and these formulations are made according to prior art methods. The formulation labelled OxPVF3, on the other hand, is a formulation according the present invention. Table 1 also details which phase or phases are produced from each of the formulation when they are made to form films.

TABLE 1

| FORMULATION | | | | | FILMS FORMED | | | PV |
|---|---|---|---|---|---|---|---|---|
| OxPVF # | $PbCl_2$ | $PbI_2$ | FAI | MAI | delta | alpha | $PbI_2$ impurity | performance |
| 0 | | 1 | 1 | | Yes | Yes | Yes | Low |
| 1 | 1 | | 3 | | Yes | Yes | Yes | Low |
| 2 | | 1 | 1 | 2 | Yes | — | — | Low |
| 3 | 1 | | 1 | 2 | — | Yes | — | High |

| # | $PbCl_2$ | $PbI_2$ | FAI | MAI | | | | |
|---|---|---|---|---|---|---|---|---|
| | | 1 | | 3 | Reference MA formulation | | | |

Figure 2:
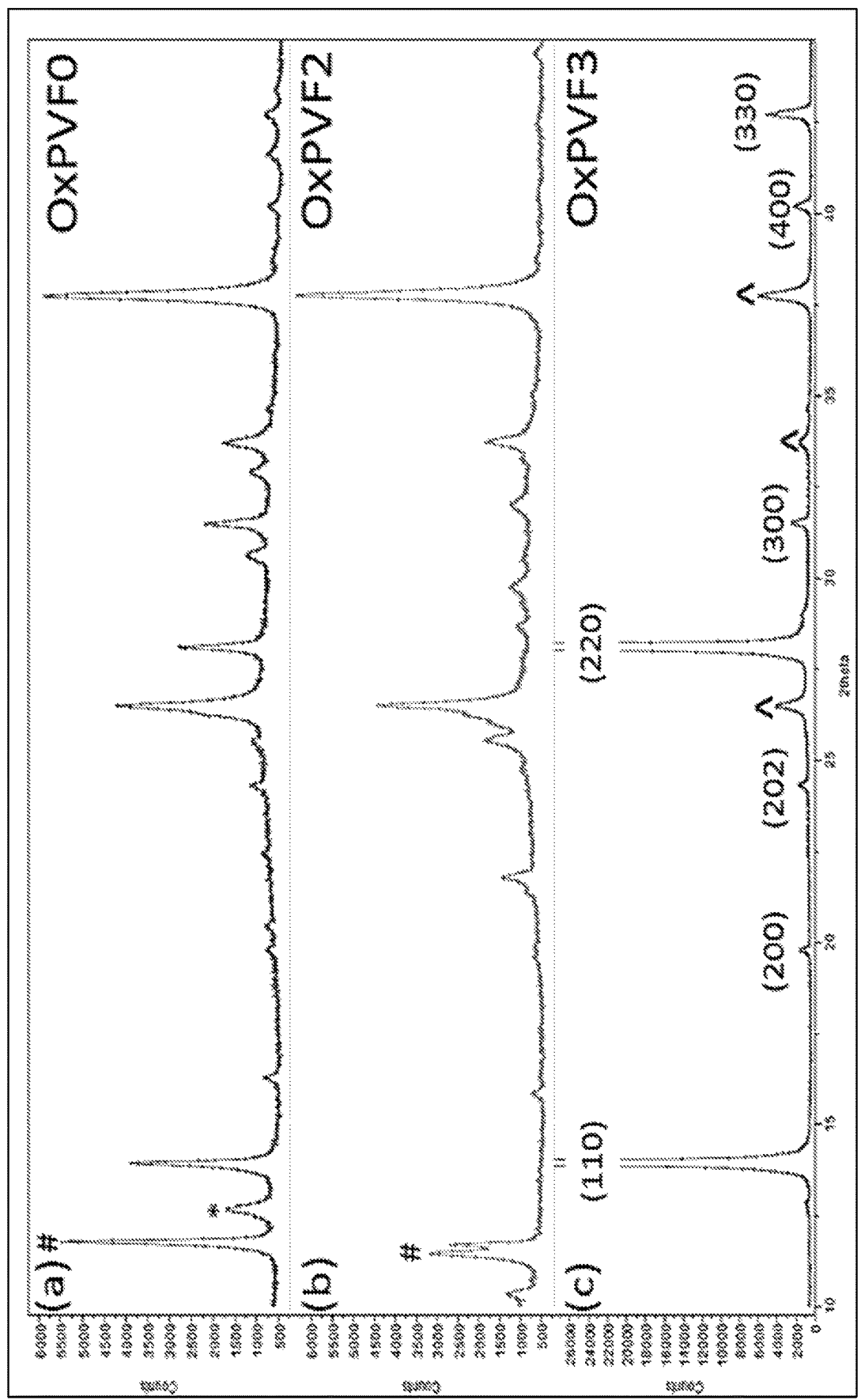
FIG. 2 shows XRD traces of $FAPbI_3$ films produced from (a)1:1 stoichiometric ratio of $PbI_2$ and FAI; (b) 1:1:2 ratio of $PbI_2$:FAI:MAI and (c) OxPVF3 precursor formulations. The numbered peaks correspond to the alpha phase perovskite and the peak labels #, *, ˆ, denote delta polymorph, $PbI_2$ and FTO respectively.

As the XRD shown in FIG. 2 the OxPVFO formulation yields both the alpha and delta FAPbI$_3$ phase when using the 1:1 stoichiometric precursor solution, together with a large percentage of PbI$_2$ impurities remaining within the film. The OxPVF1 formulation results in a mixture of the two phases (the film is orange in appearance) and lead halide impurities, and the OxPVF2 formulation comprising the 1:1:2 ratio of PbI$_2$:FAI:MAI, produces only the delta FAPbI$_3$ perovskite. The residual Pb halide peak is no longer present.

The OxPVF3 formulation according to the present invention includes both FAI and MAI in the precursor formulation, as well as chlorine and iodine, and as confirmed by the XRD this aids the selective formation of the alpha perovskite in thin films and leaves no residual lead halide within the films.

The cell parameters for the perovskite film formed form formulation OxPVF3 according to the invention were calculated to be a=9.01335 Å, c=10.92557 Å and is largely in agreement with literature for the pure FAPbI$_3$ perovskite (a=8.9920 Å, c=11.0139 Å). Although the c-axis is marginally smaller than literature, the a-axis has increased suggesting a slightly different orientation or strain on the structure, perhaps influenced by the substrate. If there was inclusion of the MAI cation into the structure, both cell parameters would be expected to decrease. It has been shown by the Applicants that in a stoichiometric mix of the two cations, MA$_{0.5}$FA$_{0.5}$PbI$_3$ perovskite bulk powder the cell parameters are; a=8.84986 Å c=10.9513 Å.

Figure 3:
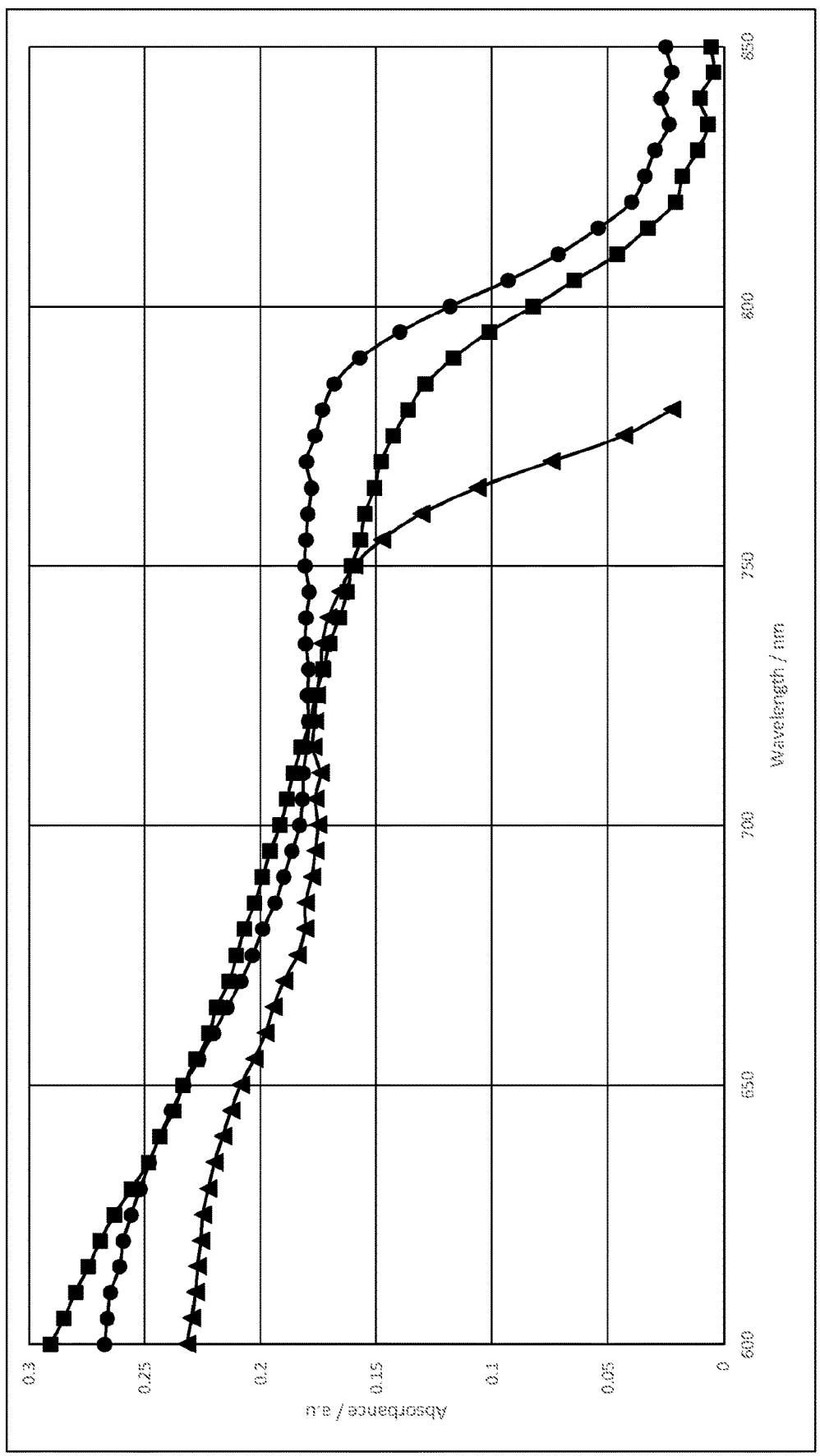
FIG. 3 shows the Absorbance spectra for perovskite films deposited on FTO/c-$TiO_2$ formed from either, $MAPbI_3$ precursor solution (▲), 1:1 $PbI_2$: FAI precursor solution (■) or from OxPVF3 (●).

The formation of the FAPbI$_3$ is also confirmed by the band onset measured by UV-vis spectroscopy which is ~830 nm ($E_g$~1.49 eV) for the OxPVF3 formulation compared to 815 nm ($E_g$~1.52 eV) for the PbI$_2$:FAI stoichiometric formulation. MAPbI$_3$ has a band onset of 780 nm ($E_g$~1.59 eV). FIG. 3 provides a comparison of the absorbance spectra for perovskite films deposited on FTO/c-TiO$_2$ for MAPbI$_3$ precursor solution (▼), PbI$_2$:FAI precursor (■) and OxPVF3 (●).

The proposed mechanism of OxPVF3 for the formation of the FAPbI$_3$ is as follows:

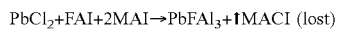
PbCl$_2$+FAI+2MAI→PbFAI$_3$+↑MACl (lost)

It is be expected that the lower molecular weight "cation+halide ion" would be sacrificed and exit the film. Where the "cation+halide ion" is MACl this would be expected to leave the film at temperatures >80° C. In this regard, the order of volatility: MACl>FACl>FAI Current ratios that predominately form the alpha phase are:

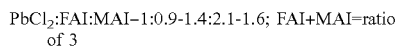
PbCl$_2$:FAI:MAI~1:0.9-1.4:2.1-1.6; FAI+MAI=ratio of 3

Mixtures of Pb halides could also be used. For example:

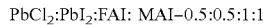
PbCl$_2$:PbI$_2$:FAI: MAI~0.5:0.5:1:1

Once the precursors are mixed in solution, variations with the formulation can also exist such as:

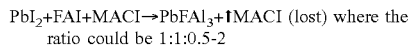
PbI$_2$+FAI+MACl→PbFAI$_3$+↑MACl (lost) where the ratio could be 1:1:0.5-2

The perovskite requires the ratio of Pb to FAI to halide X in the final perovskite to be 1:1:3 where the halide contribution could be a mixture of X=F, Br, Cl, I. For example:

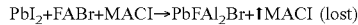
PbI$_2$+FABr+MACl→PbFAI$_2$Br+↑MACl (lost)

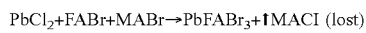
PbCl$_2$+FABr+MABr→PbFABr$_3$+↑MACl (lost)

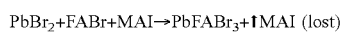
PbBr$_2$+FABr+MAI→PbFABr$_3$+↑MAI (lost)

The methylammonium cation can also be replaced with cations smaller than formamidinium such as ammonium (NH$_3^+$) and be sourced from NH$_4$Cl, NH$_4$Br, NH$_4$I, NH$_4$F, or Cs sourced from CsCl, CsI, CsBr, CsF. There is also the possibility for mixed cation based perovskites which predominately form the alpha phase perovskite.

Figure 4:
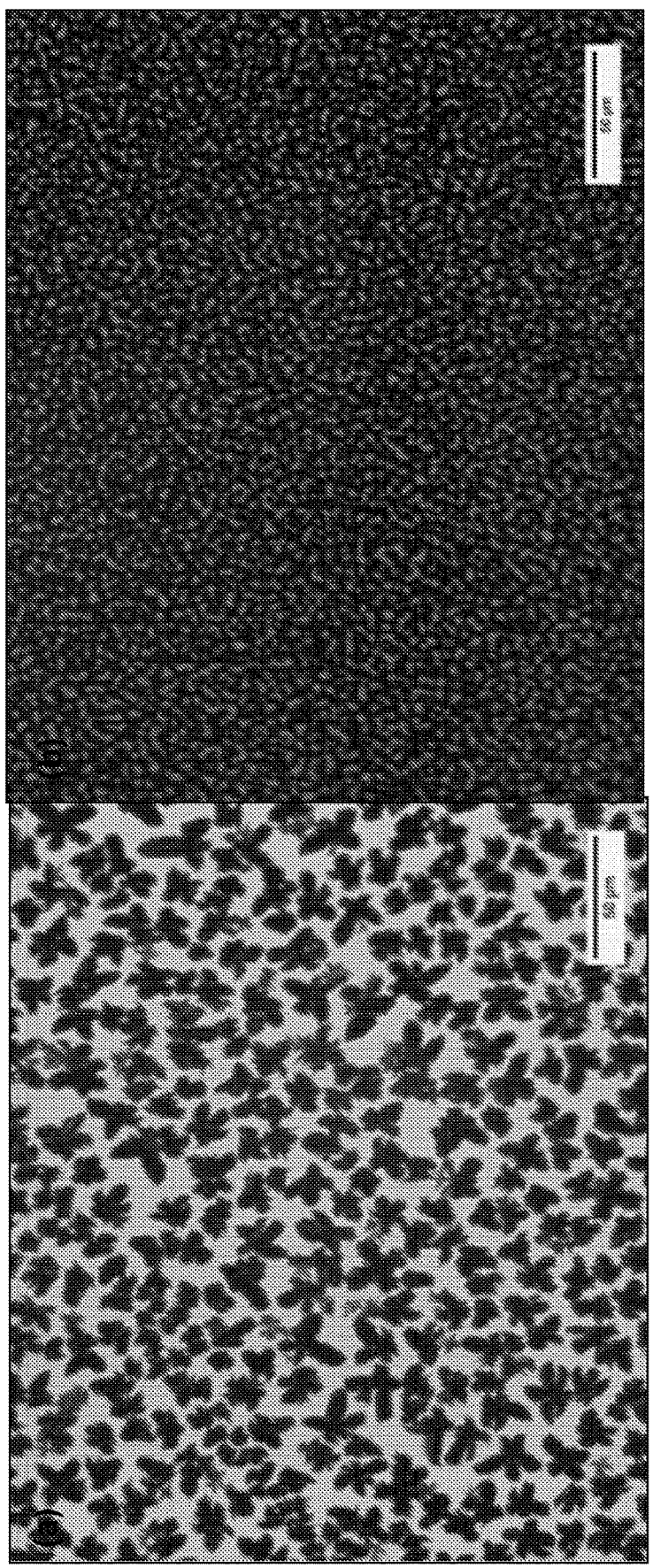
FIG. 4 shows Optical microscopy at 40× magnification of (a) OxPVF3 in DMSO and (b) OxPVF3 in DMF deposited onto FTO/c-$TiO_2$. Scale bar 50 µm.
Figure 5:
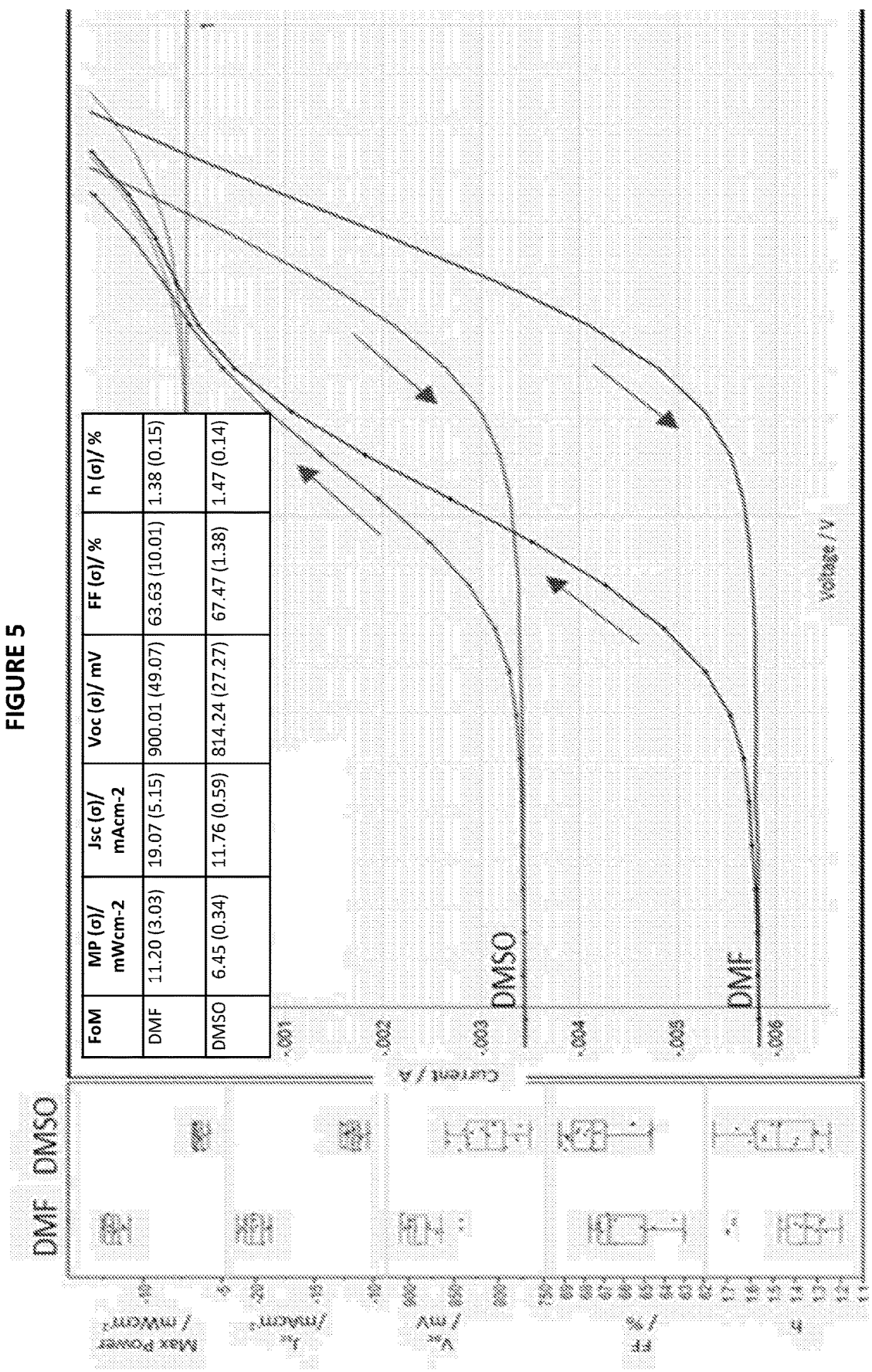
FIG. 5 shows the figures of merit and current—voltage (IV) curves for typical semi-transparent $FAPbI_3$ on compact $TiO_2$ devices measured under 1 sun of AM1.5 solar irradiation. Arrows indicate forward (SC to OC) and reverse (OC to SC) scans. Tabulated information is for OC to SC.

Investigation of the Influence of Solvent in Creating Both High Coverage and Low Coverage for Various Architectures as Substantiated with the Following Data Shown in FIG. 4 are the different morphologies of the OxPVF3 formulation according to the invention when used in different solvents. When used in high boiling point solvents, such as DMSO, the resulted films have a surface coverage of ~65%, ideal for use in semi-transparent cell architectures (FIG. 4a). Whereas, when used in low boiling point solvents, such as DMF the resultant film has a much larger surface coverage of 85%, lending itself to use for continuous opaque perovskite cells (FIG. 4b).

There is also great potential for mixtures of solvents to be used to influence the morphology of the perovskite films further to optimise for various cell architectures and larger scale coating procedures such as slot die, screen printing etc.

Table 2 is a summary of the range of curing parameters for OxPVF3 to form the FAPbI$_3$ perovskite films.

| Curing Parameters | |
|---|---|
| Temp/° C. | Time/mins |
| 80 | 120 |
| 100 | 60 |
| 150 | 30-60 |
| 170 | 10-20 |

Photovoltaic Performance
a. Planar Structures

The figures of merit (FOM) and current-voltage (IV) curves of the FAPbI$_3$ formed from OXPVF3 (cured at 150° C. for 30 mins) research cells are shown in Error! Reference source not found.5.

It is apparent that the formulation solvent is extremely important in terms of device performance. This change in solvent can produces high surface coverage films when using a DMF formulation, resulting in an average P$_{max}$ of 11.2 mW cm$^{-2}$ or discontinuous films for semi-transparent architectures when using DMSO in the precursor formulation achieved an average P$_{max}$ of 6.5 mWcm$^{-2}$.

b. Meso-porous Structures

The presence of both MAI and FAI in mixed cation perovskites on mesoporous titania is already known in the prior art and such compounds were prepared in a two-step deposition process requiring a thin film of lead iodide to be deposited onto the mp-titania under inert atmosphere and then subsequently immersed into the FAI/MAI mix (in IPA). When using only FAI, this resulted in the predominant appearance of the delta phase. By addition of MAI to the FAI mix, the delta phase was reduced with increasing MAI content and appearance of a black perovskite was produced. The band gap suggests a mix of FA and MA into the structure, with the XRD inconclusive as to the percentage of each perovskite material formed. There is also still a percentage of unreacted PbI$_2$ left over during this process with is detrimental to device performance.

By contrast, the OxPVF3 precursor of the present invention allows the preferential formation of the alpha FAPbI$_3$ polymorph within a mesoporous (mp-) scaffold from a single precursor solution, something so far not achieved by academic groups working on FAPbI$_3$. Most groups resort to using the two-step deposition process which still incurs delta phase and lead iodide impurities. The single precursor method of the present invention reduces both the existence of the delta polymorph and lead iodide impurities, the requirement for extra steps and it is highly suited to the use of ambient processing conditions.

Figure 6:
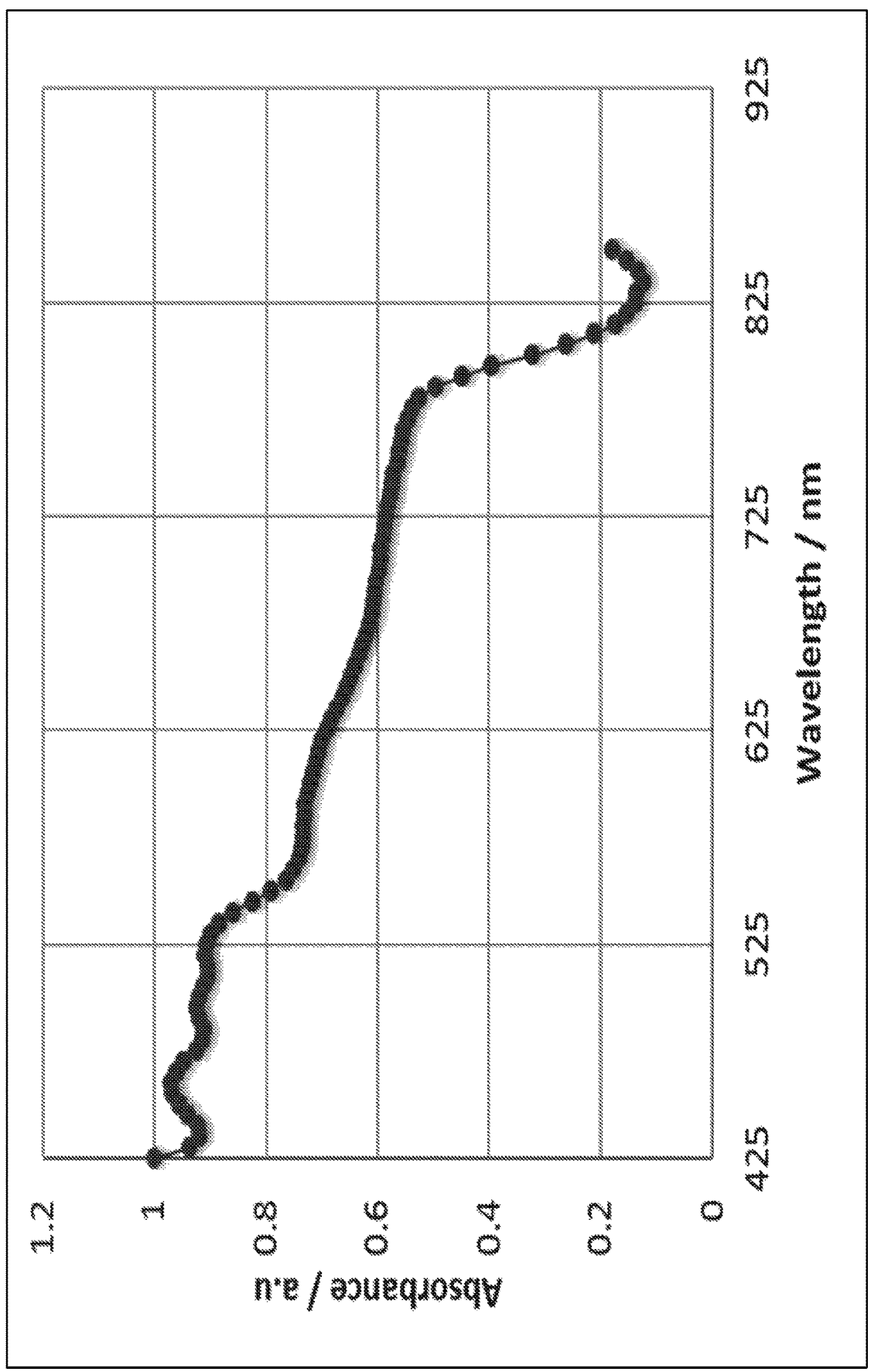
FIG. 6 shows the absorption spectra for OxPVF3 deposited on FTO/c-$TiO_2$/mp-alumina.

The formation of the $FAPbI_3$ perovskite is confirmed by the absorption spectra and band onset of ~825 nm (Eg~1.5 eV) shown in FIG. 6 when deposited on mp-alumina.

Figure 7:
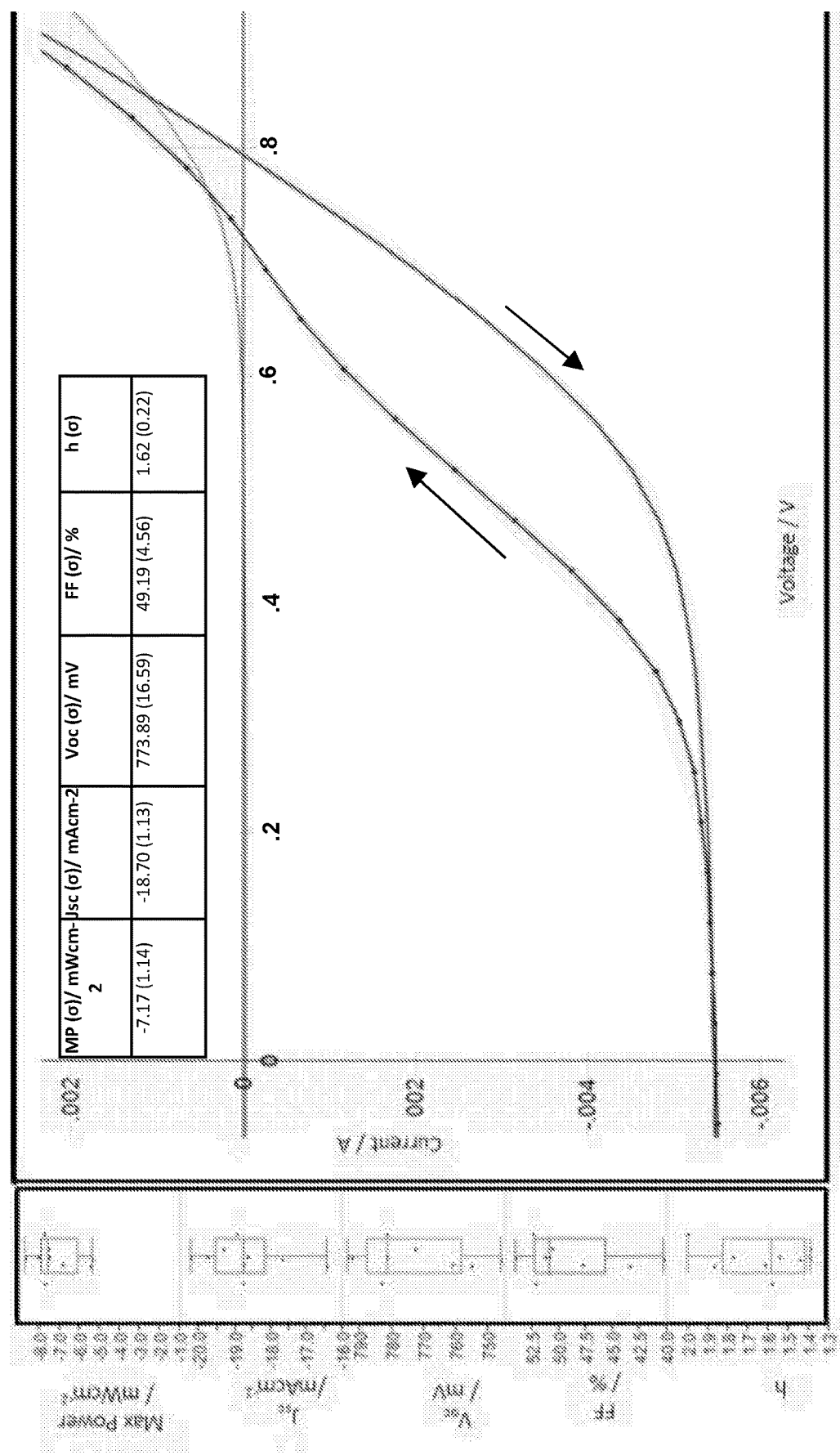
FIG. 7 shows the Figures of merit and current—voltage (IV) curves for $FAPbI_3$/mp-$Al_2C_3$ devices processed from OxPVF3 measured under 1 sun of AM1.5 solar irradiation. Arrows indicate forward (SC to OC) and reverse (OC to SC) scans. Tabulated information is for OC to SC.

Un-optimised cell results are also shown in FIG. 7 (films cured at 150° C. for 30 mins).

Although un-optimised at only ~7 $mWcm^{-2}$, with scaffold and contact optimisation this structure could allow for an improvement over the conventional $MAPbI_3$/mp-alumina cells in terms of both cell performance (due to the increase in absorbance achieved by the reduction in band gap) and long term stability of the $FAPbI_3$ perovskite (due to its greater thermal stability).

To conclude, the results for the formulations of the present invention demonstrate that the use of a three component formulation containing a first organic cation, A (e,g, a formamidinium halide) alternative cation, A' (e.g. methylammonium halide) and a metal, M source (e.g. lead halide) a first anion, X (e.g. a halide) and an alternative anion X' (e.g. another halide), is able to preferentially form the alpha phase of the formamidinium perovskite and minimal to zero metal halide impurities remaining within the film. Moreover, this is demonstrated as possible under ambient conditions and by using a one-step deposition process, allowing for ease of fabrication whilst still retaining a phase purity of >99%. The formulation according to the present invention also allows for the deposition onto mesoporous scaffolds such as mesoporous alumina which so far has eluded the perovskite device community. This concept can be transferred to allow phase pure mixed halide formamidinium perovskites, using a variety of precursors and sacrificial ions, which enables band gap tuning of the formamidinium without high levels of phase impurities causing detrimental effects to the cell performance.

It will be appreciated that individual items described above may be used on their own or in combination with other items shown in the drawings or described in the description and that items mentioned in the same passage as each other or the same drawing as each other need not be used in combination with each other.

Furthermore, although the invention has been described in terms of preferred embodiments as set forth above, it should be understood that these embodiments are illustrative only. Those skilled in the art will be able to make modifications and alternatives in view of the disclosure which are contemplated as falling within the scope of the appended claims. For example, those skilled in the art will appreciate that whilst the above-described embodiments of the invention all relate to photovoltaic devices, aspects of the invention may be equally applicable to other optoelectronic devices. In this regard, the term "optoelectronic devices" includes photovoltaic devices, photodiodes (including solar cells), phototransistors, photomultipliers, photoresistors, and light emitting diodes etc. In particular, whilst in the above-described embodiments the photoactive perovskite material is used as a light absorber/photosensitizer, it may also function as light emitting material by accepting charge, both electrons and holes, which subsequently recombine and emit light.

The invention claimed is:

1. A formulation for use in the formation of a light absorbing perovskite material having a general formula (I) of:

$$AMX_3 \qquad (I)$$

wherein A is one or more monovalent cations, M is one or more divalent metal cations, and X is one or more halide anions, the formulation comprising two or more compounds which between them comprise:
the one or more monovalent cations A;
the one or more divalent metal cations M;
the one or more halide anions X;
one or more further monovalent cations A'; and
one or more further halide anions X';
wherein the one or more further monovalent cations A' and the one or more further halide anions X' are selected to form one or more A'X'-containing compounds which are able to be fully separated from the $AMX_3$ material at a temperature of less than 200° C.

2. A formulation according to claim 1, wherein the perovskite material is black in colour.

3. A formulation according to claim 1, wherein the perovskite material has a band gap below 3.0 eV.

4. A formulation according to claim 1, wherein the formulation comprises an excess of the one or more further monovalent cations A' and the one or more further halide anions X'.

5. A formulation according to claim 4, wherein the ratio of the one or more further monovalent cations A' and the one or more further halide anions X' to the one or more monovalent cations A and the one or more halide anions X is from 1.6:1 to 2.1:1.

6. A formulation according to claim 1, wherein A is one or two monovalent cations, M is a divalent metal cation, and X is one or more halide anions, and the formulation comprises two or more compounds which between them comprise:
the one or two monovalent cations A;
the divalent metal cation M;
the one or more halide anions X;
a further monovalent cation A'; and
a further halide anion X'.

7. A formulation according to claim 1, wherein A comprises a first monovalent cation and the formulation comprises:
a first precursor compound comprising the first monovalent cation A and a halide anion X;
a second precursor compound comprising a further monovalent cation A' and a halide anion X; and
a third precursor compound comprising a metal cation M and a further halide anion X'.

8. A formulation according to claim 1, wherein A comprises a first monovalent cation Ai, and a second monovalent cation $A_2$, and the formulation comprises:
a first precursor compound comprising the first monovalent cation $A_1$ and a halide anion X;
a second precursor compound comprising a further monovalent cation A' and a halide anion X;
a third precursor compound comprising the second monovalent cation $A_2$ and a halide anion X; and
a fourth precursor compound comprising a metal cation M, and a further halide anion X'.

9. A formulation according to claim 1, wherein at least one of the one or more monovalent cations A, and the one or more further monovalent cations A', are selected from ammonium ($NH_4^+$), methyl ammonium ($CH_3NH_3^+$), formamidinium ($HC(NH_2)_2^+$), methylformamidinium ($H_3CC(NH_2)_2^+$), guanidinium ($C(NH_2)_3^+$), tetramethylammonium ($(CH_3)_4N^+$), dimethylammonium ($(CH_3)_2NH_2^+$) and trimethylammonium ($(CH_3)_3NH^+$), $Cs^+Rb^+$, $Cu^+$, $Pd^+$, $Pt^+$, $Ag^+$, $Au^+$, $Rh^+$, and $Ru^+$.

10. A formulation according to claim 1, wherein A comprises any of:
  methyl ammonium ($CH_3NH_3^+$) and formamidinium ($HC(NH_2)_2^+$);
  formamidinium ($HC(NH_2)2^+$) and $Cs^+$; and
  formamidinium ($HC(NH_2)_2^+$).

11. A formulation according to claim 10, wherein A' comprises one or more of ammonium ($NH_4^+$) and methyl ammonium ($CH_3NH_3^+$).

12. A formulation according to claim 1, wherein M comprises one or more of $Pb^{2+}$, $Sn^{2+}$, and $Bi^{2+}$.

13. A formulation according to claim 1, wherein X comprises one or more halide anions selected from fluoride, chloride, bromide, and iodide.

14. A formulation according to claim 1, wherein X' comprises one or more halide anions selected from fluoride, chloride, bromide, and iodide.

15. A precursor solution for use to make a perovskite material of the general formula $AMX_3$, said precursor solution comprising a suitable solvent system and two or more compounds which between them comprise one or more first cations A; one or more metal cations, M; one or more second cations A'; one or more first anions X and one or more second anions X'; and further wherein the ratio of ions is selected such that A:M:X is 1:1:3, and the amount of and choice of the one or more second cations A' and second anions X' is selected to form one or more A'X'-containing compounds which are able to be fully separated from the $AMX_3$ material at a temperature of less than 200° C.

16. A precursor solution according to claim 15, and comprising a solvent system comprising one or more solvents selected from dimethyl sulfoxide (DMSO), N,N-dimethylformamide (DMF), N-cyclohexyl-2-pyrrolidone (CHP), and dimethylacetamide (DMAc).

* * * * *